United States Patent
Hoctor et al.

(10) Patent No.: US 8,574,157 B2
(45) Date of Patent: Nov. 5, 2013

(54) METHOD AND APPARATUS FOR GENERATING AN ULTRASOUND IMAGE OF MOVING OBJECTS USING DEFORMABLE MODELS

(75) Inventors: Ralph Thomas Hoctor, Saratoga Springs, NY (US); Mirsaid Seyed Bolorforosh, Guilderland, NY (US); Bruno Hans Haider, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 1672 days.

(21) Appl. No.: 11/674,854

(22) Filed: Feb. 14, 2007

(65) Prior Publication Data

US 2008/0194957 A1 Aug. 14, 2008

(51) Int. Cl.
*A61B 8/00* (2006.01)

(52) U.S. Cl.
USPC ........... 600/443; 600/407; 600/437; 600/447; 600/450; 382/128; 382/164; 128/916; 703/11

(58) Field of Classification Search
USPC .................. 600/443, 447, 450; 382/128, 164; 128/916; 703/11
See application file for complete search history.

(56) References Cited

U.S. PATENT DOCUMENTS

| | | | |
|---|---|---|---|
| 5,997,479 A * | 12/1999 | Savord et al. | 600/447 |
| 6,216,027 B1 | 4/2001 | Willis et al. | |
| 6,248,070 B1 | 6/2001 | Kanda et al. | |
| 6,295,464 B1 | 9/2001 | Metaxas | |
| 6,701,174 B1 | 3/2004 | Krause et al. | |
| 6,950,689 B1 | 9/2005 | Willis et al. | |
| 8,094,772 B2 | 1/2012 | Grass et al. | |
| 2003/0036083 A1 | 2/2003 | Tamez-Pena et al. | |
| 2004/0122320 A1 * | 6/2004 | Murashita | 600/449 |
| 2006/0247864 A1 * | 11/2006 | Tamez-Pena et al. | 702/19 |
| 2008/0181479 A1 * | 7/2008 | Yang et al. | 382/131 |

FOREIGN PATENT DOCUMENTS

| | | |
|---|---|---|
| EP | 0961135 A1 | 12/1999 |
| JP | 2000023984 A | 1/2000 |
| JP | 2000139917 A | 5/2000 |
| JP | 2004535871 A | 12/2004 |
| JP | 2009519801 A | 5/2009 |
| WO | 2006043238 A1 | 4/2006 |

OTHER PUBLICATIONS

Notice of Allowance from corresponding JP Application No. 2008-031208 dated Apr. 23, 2013.

* cited by examiner

*Primary Examiner* — Unsu Jung
*Assistant Examiner* — Joseph M Santos
(74) *Attorney, Agent, or Firm* — Jenifer Haeckl

(57) ABSTRACT

A method for producing a three-dimensional image (70) of an object. The method includes providing a model (8) of the object (62) (200), insonifying regions of the object from source transducers (58) external to the object (62) (202), receiving return echoes from the object (62) at receiving transducers (58) external to the object (62), processing the return echoes (204) and generating a hybrid image (70) of the object (62) comprising object regions responsive to the model (8) of the object (62) and object regions responsive to the return echoes (208/212).

60 Claims, 2 Drawing Sheets

METHOD AND APPARATUS FOR GENERATING AN ULTRASOUND IMAGE OF MOVING OBJECTS USING DEFORMABLE MODELS

FIELD OF THE INVENTION

This invention relates generally to medical diagnostic ultrasound imaging and in particular to the use of deformable models in conjunction with ultrasonic imaging.

BACKGROUND OF THE INVENTION

A conventional ultrasound imaging system includes an array of ultrasonic transducers that transmit an ultrasound wave (a transient pressure wave) during a transmit mode and receive a reflected wave reflected from an object under study during a receive mode. The spatial response to this ultrasound wave is referred to as an ultrasound beam. In general, the overall (two-way) beam is a combination of two separate beams: a transmit beam, which represents the degree to which energy is deposited in the object, and a receive beam, which represents a system response to echoes originating at various points in space. The signals generated by the transducers responsive to the received pressure wave are processed and the results displayed as a visual image of the object.

The array typically includes a multiplicity of transducers configured as a linear array or row, each transducer driven by a separate signal voltage during the transmit mode. Selecting a time delay (relative to a reference time) for the signal voltage applied to each transducer controls a direction of the ultrasonic beam energy transmitted by the individual transducers. In addition, controlling the amplitude of the signal voltage applied to each transducer can be used to lower energy present in sidelobes of the ultrasound beam.

Controlling the time delay steers the ultrasonic energy emitted by the transducers to produce a net ultrasonic wave that travels along (scans) the object in a desired direction or along a scan line (also referred to as an A-line), with the energy focused at a selected point on the scan line. That is, the transmit energy is focused or concentrated at a fixed range (fixed focal point) from the transducer array, maximally localizing the energy at that range. At other ranges (distances from the transducer array) the energy is localized to a lesser extent, producing a broader beam. Thus although the energy is focused at only a single point on the scan line, the energy at proximate points (the points comprising a focal zone) may be sufficient to produce a reflected beam that can be processed to render an image with sufficient lateral resolution.

Similar beam-combining principles are employed when the transducers receive the reflected ultrasonic energy from the scan line. The voltages produced at the receiving transducers are controllably delayed and summed so that the net received signal response is primarily representative of the ultrasonic energy reflected from a single focal zone along the scan line of the object.

To generate a two dimensional or planar image of the object (and recognizing that ultrasound imaging occurs in the near field), during the receive mode the transducers are dynamically focused at successive ranges from the transducer array (depths into the object being scanned) along the scan line as the reflected ultrasonic waves are received. The focused range is based on the round-trip travel time of the ultrasound pulse. Controlling the time-delay associated with each transducer focuses the received energy at the desired time-variant range or depth. Such dynamic focusing in the receive mode produces a usable response at the focal point and a range of distances near the focal point. The range over which the two-way response of the system is well-focused is referred to as the depth of field. Outside the depth of field the image quality suffers and the reflections are not usable to produce the image.

As can be appreciated, the instantaneous beam steering and signal combining capabilities of the linear transducer array are capable of producing only a 2D image of the object, where the image is in the plane normal to the array surface and contains the centers of the array elements.

The planar two-dimensional image formed by the standard linear transducer array can typically be updated tens of times per second. The update rate is limited by the time required for the transmitted ultrasound pulse to travel to and back from the farthest image range point (the round-trip travel time). In an echocardiogram application, for example, the update rate (also referred to as the frame rate) determines the fidelity with which motion of the heart can be depicted. A frame rate of about 30 frames per second produces the effect of real-time motion, including real time motion of the heart. Higher frame rates are required only in special diagnostic situations.

The pulse travel time (and therefore the frame rate) is further dependent on the speed of sound through the imaged tissue. Assuming a typical 70-degree sector image including 128 separate ultrasound scan lines imaged to a depth of 10 centimeters, the time interval between successive image frames (frame updates) must be long enough to permit the sound pulse to travel a distance of:

$$128 \times 10 \text{ cm} \times 2 = 2560 \text{ cm} = 25{,}600 \text{ mm}.$$

The speed of sound in tissue is about 1.54 mm/μsec, therefore at least 16.62 milliseconds must be allowed for acquisition of the data to construct a single frame in the exemplary application. Since a frame rate of 30 frames per second allows 33.3 milliseconds to acquire each frame, the exemplary scenario can easily generate images at the desired rate of 30 frames/second.

Certain ultrasound imaging systems generate multiple transmit focal zones, i.e., where the transmit beam is focused at different ranges during the transmitting mode. This practice may limit the frame update rate. Ultrasound images are formed by combining the reflected energy from the multiple focal zones into a single image (or frame) focused at all ranges. The use of such multiple transmit focal zones requires that multiple beams be formed in each insonified direction during each image scan, possibly requiring reducing the frame below the desired 30 frames per second.

Real-time, three-dimensional ultrasound images (referred to as 4D images) are formed with a planar transducer array with each real time image frame including a volumetric 3D image. Such images have been commonly produced and displayed for obstetrics applications. More recently, such images have been introduced in echocardiology.

Although it is desired to provide such volumetric 3D images in cardiology applications, the frame rate limitations in real-time 3D imaging do not allow sufficient time to insonify the entire heart volume (also referred to as a source volume), receive and process the echoes and reproduce the real time image therefrom. For example, assume in a 3D image it is desired to image 128 planes with 128 lines per plane to produce the desired image volume. The acquisition of 16,384 (128×128) lines of ultrasound data to a depth of 10 cm requires more than two seconds. Thus the desired frame rate of 30 frames per second cannot be maintained.

To overcome the acquisition time penalty and produce displays with information comparable to 2D images, it is known to construct biplane images in lieu of real time 3D volumetric images. In this display mode two orthogonal planes are insonified and the resulting images displayed. These two images are easily formed using a planar array, since the array can be beam steered in any direction, while requiring only twice as many ultrasound lines as the standard image. Thus the desired high frame rates can be achieved. With some practice, an operator can mentally construct a 3D image of the heart from the two biplane images, but this is very difficult for the novice or occasional user.

It is also known to accelerate ultrasound imaging acquisition using beam multiplexing. According to this scheme, a single, wide main lobe transmit beam is formed and multiple parallel receive beams record the echoes generated by the acoustic energy in the main beam. When there are N receive beams for each transmit beam the process is referred to as N-to-1 beam multiplexing. The resulting two-way response is the product of the receive beam and the transmit beam. If the receive beam pattern is entirely within the main lobe of the transmit beam, then the overall response is simply the receive beam pattern since the transmit main lobe energy is relatively constant. This is referred to as a one-way beam pattern.

The side lobe energy of the one way beam will be higher, in general, than the side lobe energy of the two-way beam pattern, for which the transmit and receive side lobes occur in the same directions and therefore attenuate each other.

If the side lobe energy of the one-way response is normalized to the maximal one-way response, which is at the peak of the main lobe, then the products of the sidelobes of the transmit and receive beams (which individually represent responses less than unity) are lower than the sidelobes of the receive beam alone. Even though the sidelobes of the two-way beam pattern are in the same direction, the two-way side lobe response is lower relative to the maximal main response of the two-way beams.

One approach to volumetric echocardiology imaging synchronizes image acquisition to an EKG (electrocardiogram) and collects only a quarter of the 3D volumetric imaging during each heart cycle using 4-to-1 beam multiplexing. That is, during each heart cycle three-quarters of the displayed image is taken from a recording of one of three prior heart cycles. Only one-quarter of the displayed image is a real-time image. While there are certain known disadvantages with this approach, it can produce images at an adequate frame rate.

Given the current limitations in the art, there is clearly a need for a technology that allows high frame rate visualization of a volumetric cardiac image using an ultrasound planar array.

Deformable models are known in the art and were first used in computer animation to produce realistic motion of an elastic object. A deformable model models elastic object surfaces using connected mass elements according to various physics-based or geometric techniques. As illustrated in FIG. 1, an object surface 8 is modeled as grids of point masses 10. Each mass is connected to one or more adjacent masses by a rigid elastic rod 12 that exerts a return force on the connected masses when bent, stretched or compressed away from its rest state. Different masses can also be connected by other exemplary connecting rods.

The dynamics of the surface 8 can be defined at each mass by a force balance equation such as:

$$\underbrace{m\ddot{x} + k\dot{x}}_{\text{forces from object dynamics}} + \underbrace{\delta E(x)}_{\text{internal force}} = \underbrace{f_{user}}_{\text{external force}}$$

where x is a position vector of the masses, m is the mass of each point or particle, k is a viscous friction constant (often assumed to be zero) and the variational symbol δE(x) is a restoring force proportional to the local curvature of the surface at the location of the point mass. The dots represent vector component-wise time derivatives. The variable x and the x-dot variables are vectors in a three dimensional space that describe the instantaneous condition (location, velocity, acceleration, etc.) of the model at any instant in time. Generally, the state equations defining the deformable model are derived from the force balance equation and consist of state variables and their derivatives.

This equation depicts the balance of forces resulting from motion of the point masses, restoring forces arising from the curvature of the surface at the location of the point mass and external forces controlling motion of the modeled object. For the computer animation application, external forces are specified by the animator. For medical image analysis, the external forces arise from a potential field derived from the image. In an ultrasound image, for example, the masses are attracted to regions of the image that depict strong echoes, but are not attracted to dark regions of the image depicting relatively weak echoes. That is, the echo magnitude is regarded as a type of charge and the oppositely charged point masses of the image boundaries are attracted to it.

The model set forth in the equation above allows the state variables (e.g., acceleration, velocity and position of the masses) to evolve in response to the various forces that act on them. This evolution is simulated by a discrete-time computational process in which the continuous-time state transition matrix associated with the equations of motion above is integrated to form a discrete time system matrix. Each time a multiplication of the state vector by this matrix is performed, new external force information can be incorporated into the computation as a discrete time driving function. The details of such discrete time systems are well known. For example, consult Digital Control of Dynamic Systems, by G. F. Franklin and J. D. Powell (Addison Wesley, 1980).

BRIEF DESCRIPTION OF THE INVENTION

One embodiment of the present invention includes a method for producing a three-dimensional image of an object. The method includes providing a model of the object, insonifying regions of the object from source transducers external to the object, receiving return echoes from the object at receiving transducers external to the object, processing the return echoes and generating a hybrid image of the object comprising object regions responsive to the model of the object and object regions responsive to the return echoes.

Another embodiment of the invention includes an ultrasonic imaging apparatus for producing an image of an object. The apparatus includes a plurality of ultrasonic transducers for generating ultrasonic energy, for receiving echoes from the object and for generating signals responsive to the echoes, a processor for updating at least a portion of an object model according to the signals and a display for displaying a hybrid image of the object responsive to the object model, including the portion updated according to the signals.

BRIEF DESCRIPTION OF THE DRAWINGS

The present inventions can be more easily understood and the advantages and uses thereof more readily apparent when the following detailed description of the present inventions is read in conjunction with the figures wherein.

In accordance with common practice, the various described features are not drawn to scale, but are drawn to emphasize specific features relevant to the inventions. Like reference characters denote like elements throughout the figures and text.

DETAILED DESCRIPTION OF THE INVENTIONS

Figure 1:
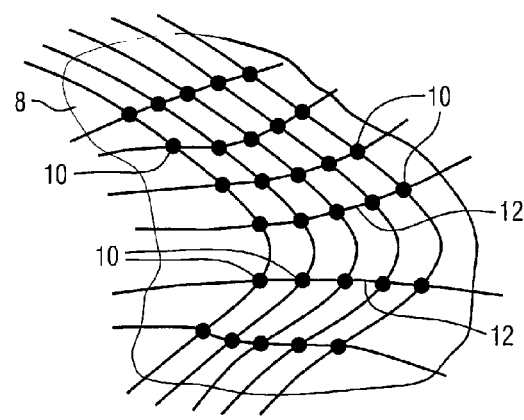
FIG. 1 illustrates a portion of a surface of a deformable model according to the prior art.

Before describing in detail the particular method and apparatus related to use of deformable models in 3D ultrasound imaging, it should be observed that the embodiments of the present inventions reside primarily in a novel and non-obvious combination of elements and process steps. So as not to obscure the disclosure with details that will be readily apparent to those skilled in the art, certain conventional elements and steps have been presented with lesser detail, while the drawings and the specification describe in greater detail other elements and steps pertinent to understanding the inventions.

The presented embodiments are not intended to define limits as to the structures, elements or methods of the inventions, but only to provide exemplary constructions. The embodiments are permissive rather than mandatory and illustrative rather than exhaustive.

When a deformable model is used for static segmentation of a still image in the prior art, the external driving force derived from the potential field is generally more important than the dynamics of the model's surface. For medical image analysis, the external forces arise from a potential field derived from the acoustic echoes received from the object and used to form the image. In an ultrasound image, for example, the masses of the model are attracted to regions of the image formed by strong echoes and are not attracted to dark regions of the image depicting relatively weak echoes. Thus the echo magnitude is regarded as a type of charge and the oppositely charged point masses of the object are attracted to it.

Application of the deformable model to the static segmentation application requires only that the model's final configuration represent an equilibrium position of the surface in the external potential field generated by the image. The model's transient response can be any response that is convenient to the model designer. The fastest static model response occurs when the model points have very low mass, minimizing the effects of object dynamics. (This type of response also eliminates overshoot and the resulting oscillations that can occur in linear systems. Such oscillations tend to slow the model's response to the potential field.) In effect, the deformable model absent consideration of the object dynamics, is simply a method for managing a constrained optimal fit of the model to the image. The constraint is a smoothness constraint and is represented by the elastic return forces of the model. The objective function is a measure of the fit of the model to the image and is represented by the potential energy field as derived from the image. This is also the case when tracking a surface using a sequence of complete images, since every image can be fit separately, presumably using constraints derived from images taken at about the same time to ensure a smooth evolution of the model shape through the image sequence.

In contrast to the use of deformable models in the prior art, the present inventions use model components of non-negligible mass so that the model's shape and position can continue to evolve in the absence of external forces. This allows the model to track the motion of the heart over short periods of time when only sparse image data is available.

When forming a real-time 3D ultrasound image of a heart there is not enough time to insonify the entire source volume to produce complete 3D frames at a sufficiently high rate to depict heart motion. To overcome this limitation, one embodiment of the invention forms an animated image of the heart (or another source volume or object) based on currently available (real time) image data (responsive to return echoes from the insonified regions) of a portion of the source volume, with remaining portions of the source volume rendered according to its deformable model. Thus a complete 3D image (which may be referred to as a hybrid image since certain portions of the image are formed from real time echoes from the object and other portions are formed responsive to the deformable model.) is produced at the desired frame rate. The ability to display echocardiology heart images in real time at the desired frame rate, as provided by the present inventions, allows analysis of the moving heart and its characteristics, including shape, velocity and acceleration.

The overall deformable model of the heart includes linked models of interior heart chambers and the myocardium exterior. Each heart chamber also has its own closed-surface deformable sub-model, with the sub-models joined by elastic connectors to ensure they exhibit the correct spatial relationship to each other. In one embodiment of the model, areas of echogenicity (areas that create a return echo when insonified) between the interior (chamber) and exterior (heart) boundaries of the myocardium will not generate a potential field because the model connectors between the interior and exterior walls tend to make the walls as thin as possible. But echoes from myocardium regions outside the space between the interior and exterior walls will influence the shape and position (orientation) of the model to conform to the image information. Echoes from regions inside the space between the interior and exterior walls indicate a shape or position that is not different from the present shape or position of the model and so are not processed.

The model connectors allow for expansion and contraction of exterior heart wall thickness, especially in the region of the ventricles. The equilibrium state of the model will comprise a highly reflective material for the model regions of the myocardium, thus these regions are highly responsive to the return echoes.

A deformable model of the heart may consist of four closed surfaces representing, the interior walls of the four heart chambers, enclosed in a larger closed surface representing the exterior of the heart. The individual surfaces are connected to each other by rigid elastic members, similar to the connections between individual masses of the surfaces as illustrated in FIG. 1. The models of the right and left ventricles are joined together by relatively rigid connectors, representing the relative inflexibility of the ventricular septum. The connectors between the ventricle models and the exterior heart model are more elastic, allowing the myocardium to change its thickness more than the septum does. The two atrial models are adjacent and disposed over the two ventricular models.

To render an accurate image, according to an embodiment of the invention the state of the deformable model is updated by the image return data from multiple ultrasound scan lines. In one embodiment, the model is updated with return echoes from every scan line. A region of the heart (or another source volume) is insonified and the ultrasound echo data is acquired from the scan line (or a bundle of scan lines in the multiple scan case). The return data is converted to a representation suitable for application to the model, that is application to the model as a potential field or as a change in the potential field. This new field exerts an influence on the dynamics of the model (e.g., location, motion, shape of the masses and thus on the regions and surfaces including the masses) through the model's state equations, such as the state equation derived from the force balance equation set forth above, wherein the potential field is regarded as an external force exerted on the model masses and thus affects the model state variables.

The updated image information applied to the model through the potential field term will especially and immediately have an effect on the state variables associated with masses of the source volume (and the regions including those masses) that are within or spatially close to the region imaged during the scan line. Thus in effect, each model update responsive to an ultrasound A-line is a localized update to the potential field generated from the ultrasound line image data. The acoustic data from a single ultrasound scan line tends to strongly influence only a few of the many state variables of the deformable model. The state variables representing regions that are proximate the location of the scan line are most affected because the forces exerted on the masses of that region are inversely proportional to the square of the distance between the mass and the attracting image information (similar to the gravitational potential field). Only those regions of the model that are intercepted by the new scan line are updated; the potential field associated with the other regions remains unchanged.

As the external force field changes responsive to new image data, new and different forces are imposed on the masses of the model. The state variables associated with these masses are updated by a computational process that simulates the mechanical motion of the model responsive to the applied forces, that is, the forces representing the return echoes, as explained further below.

All of the return echo image data contributes to the potential field, which is a scalar function defined on space. The force exerted on a mass at any point in the space is computed as the gradient of the potential at that point. The concepts are similar to those employed in solving gravitation problems.

When two particles of masses M1 and M2 are separated by distance R, they exert an attractive force on each other given by:

$$F = -\gamma \frac{M1 M2}{R^2} \hat{e}$$

where e is a unit vector pointing in the appropriate direction and γ is a constant. In the context of the present inventions γ and the power of the parameter R are selected as desired to control the affect of the field on the model.

For continuous distributions of mass (such as the image information), the force is described as an integral over a density function defined in space.

$$F = -\gamma M1 \int_V \frac{\rho(r) e_r}{r^2} dv$$

where dv is an element of volume located at a distance r from M1 with the distributed object within the volume V. The unit vector $e_r$ points in the direction of the point mass for the given volume element. Obviously the calculated force is a vector and thus a gravitational acceleration can be defined by dividing F by M1. Accordingly, a potential field can be defined by noting that for every point in space the negative of the gradient of the potential field at that point, due to the distributed object with density ρ(x), is equal to the acceleration due to the potential field. Since only differences in potential are of interest, the constant that arises from integrating the gradient is suppressed The potential field due to a distributed object is therefore:

$$\Phi = -\gamma \int_V \frac{\rho(r)}{r^2} dv$$

and the associated force on a point of mass M1 is $$F = -M1 \text{ grad } \Phi$$

Recall that the position of M1 is implicit in the definition of the potential.

In the state variable model used with the present inventions, which is written in terms of accelerations and velocities (i.e., the first derivative of the velocity and position state variables), the acceleration computed from the potential field is used directly. (This discussion follows that of "Classical Dynamics of Particles and Systems" by J. B. Marion (Academic Press, 1970).

The technique for using the image data to update the state variables is described below. Assume that the following force balance equation governs at a given mass point:

$$m\ddot{x} + k\dot{x} + F_{model}(x) = F_{image}(x)$$

In this equation $F_{model}$ is a force derived from the distances from the particle to the adjacent particles to which it is attached and also from the degree to which that particle and its neighbors fail to lie on some surface of characteristic shape (for example, a plane or a patch of a cylinder). $F_{image}$ is derived using the potential field described above, thus $$F_{image} = m\gamma \text{ grad}\left[\int_V \frac{\rho(r)}{r^2} dv\right]$$

Rewrite the force equation in terms of the acceleration:

$$\ddot{x} = \frac{-k}{m}\dot{x} + \frac{(F_{image}(x) - F_{model}(x))}{m}$$

Define two new state variables x1=x and x2=dx/dt and rewrite the above equation as two coupled first-order differential equations:

$$\begin{cases} \dot{x}_2 = \frac{-k}{m} x_2 + A_{total}(x_1, \text{adjacent mass positions}) \\ \dot{x}_1 = x_2 \end{cases}$$

where the two force terms have been combined into an acceleration function $A_{total}$, which is a function of $x_1$ and the position of the other adjacent masses, i.e., including the image potential function and the forces due to the local state of the model. The overall state variable model is given by such a pair of equations for every point mass in the deformable model, and the equations are coupled between point masses by the dependence of the model-derived forces on the local shape of the model. Thus new state variables defining the state of the model are calculated from a combination of the model-derived forces and the image-derived forces after each ultrasonic scan of the object. These new state variables are then supplied to the image generating software where they influence the region of the image that was scanned. The displayed image is based on the current, updated version of the model state variables. In general, the values of the state variables differ throughout the model at every new data update time because of the dynamical nature of the model.

It is recognized that the image data according to the inventions may be relatively sparse since it is does not comprise a sequence of complete images of the insonified object. However the data is provided in real time and is sufficient to affect the potential field of the deformable model and thus improve the model's representation of the insonified object. The frequent infusion of new information into the model state permits a sparse update strategy, while the model closely depicts the real time state of the heart. High rate, but sparse, updates should be sufficient to limit the real time error between the predicted model and the actual heart.

The prediction error of the update process is a measure of the degree to which the model and the return ultrasonic echoes disagree. If the model predicts the exact location of the heart wall (or another heart structure) as determined by the ultrasound image data, then the prediction error should be zero. To the extent that the model fails to predict image features, the prediction error is greater than zero. The model masses are attracted to the image information through conversion of the image information to the potential field, as described above, to reduce the error between the model and the image data, ideally to reduce the error to zero. Therefore the potential energy and the resulting potential field, in effect, are proportional to the error between the model predicted location of a region or structure of the source volume and the imaged location of the region or structure. The potential energies are in fact never zero, but a zero prediction error should correspond to a local minimum of the potential field. In an embodiment where the heart model includes an inner and an outer heart wall surface for each heart chamber, the equilibrium state (i.e., minimum error) is one in which the heart wall echoes fall between the two surfaces.

Generally, the prediction error is high when echoes from an insonified region are not contained within the model's depiction of those regions. For example, when the echoes are not from within the heart wall boundaries of the model, the error associated with the heart wall boundaries tends to be high. Prediction error is low when the scan line does not contain any heart wall information or when such echoes are identified as heart wall by the location of the model boundaries. Because the inventions use potential energy to reduce prediction error, no potential energy exists if there is no image information. Thus there can be no model error if there is no potential energy in the model region of interest. But error is present if the imaging process generates potential energy associated with the model region.

If the model predicts the position of the heart walls in some region with a relatively low error rate, then that region of the source volume will be insonified relatively less frequently than a region where the prediction error is high. If there are relatively large prediction errors, the imaging process is controlled in real time to fulfill the needs of the computed model for additional data, reducing the prediction error by attracting (i.e., by generating a potential field) the model masses to the actual locations of the insonified region.

A prediction error filter (such as used in adaptive filters) can determine the beam steering directions where the prediction error is relatively high and therefore insonify those regions to reduce the error. For example, the filter can generate a map of the insonified object with the prediction errors indicated thereon. Real time feedback from the model map to the scan process directs the next scan of ultrasound energy to that portion of the object (sample volume) with the highest prediction error. For example, the scan process may be more frequently directed to those regions that are most difficult to represent with the deformable model, such as heart valves or areas of the heart wall that have suffered myocardial damage. Also, the density of scan lines in a region to be insonified can be controlled responsive to the object error map (i.e., higher density scan lines for regions of greater error).

The elastic restoring forces of the model tend to keep the object surfaces smooth and resist the tendency to "pucker up" when an isolated scan line of image data is acquired that passes through that region of the object.

The updated external force term (the potential energy or potential field) derived from each scan line decays with time, allowing older image data to fade with time, i.e., continually reducing the influence of that data on the state of the model. Preferably, the decay rate should be sufficiently high so that image data has an influence on the deformable model for a time substantially less than a heart cycle. This condition permits frequent updating of the image during a heart beat and thus a more accurate model that provides more accurate analysis of cardiac function.

Due to the mass in the model nodes, the state equation continuously predicts the model's characteristics without new data from ultrasound images (i.e., in the absence of outside forces), responsive specifically to previous wall motion and the state variables and state equations. Certain state variables that are not updated by a specific scan may continue to be updated by the decaying potential field from prior scans. Also, as subsequent scans of other regions of the object are processed the relevant model state variables will be updated. Generally, a complete image of the source volume may not be generated if the model appears to be predicting object shapes and locations correctly, such as the correct location and shape of the heart wall.

Although according to the inventions regional model information is updated faster than the desired frame rate of about 30 frames per second, global image information is updated at a rate that is too low to generate a continuous updated external force in the correct direction for every mass element of the insonified object. Thus the object dynamics, as determined by the deformable model, keep the masses moving in the direction determined by their state variables. Thus the instantaneous position of each mass particle is, to some extent, a prediction of the position (velocity, acceleration) of the heart wall and heart components based on the dynamics of the model and based on real time updates from the insonification data.

It has been determined that during each 33.3 ms frame there is sufficient time to sample about 25% of the heart volume using 4-to-1 multiplexed beams. Thus it appears that imaged data can supply enough information to update the state variables of the heart model to maintain an accurate representation of the shape of the heart, including the heart walls and other features. Thus a clinically accurate model of the insonified heart can be obtained, considering the acoustic propagation time and the desired frame rate.

Since the potential field is generated by an ultrasound image, speckle (texture) may affect the ability of the model to track the heart walls. Smoothing or morphological filtering of ultrasound amplitude data prior to the computation of the potential field may be used to address this issue. Such techniques are known in the art.

Motion of the transducer probe or rotation of the heart with respect to the probe may be problematic since such motion changes alignment between the ultrasound beam and the heart. The system of one embodiment of the invention overcomes this effect, responsive to the imaging data and the potential field created based thereon, by rotating the entire model. Since the scan line data updates about every 30 μsec, the extent of motion or rotation that can occur between data updates is limited. In addition, in one embodiment the model includes state variables dedicated to angular velocity to allow the model to rotate in space in response to probe motion or its own motion in the chest. With these state variables in place, the least energy transfer path predicted by Hamilton's principle should pass through the angular motion subspace rather than passing through the subspace of phase space associated with the linear motion of the mass particles.

In the application of deformable modeling to 3D ultrasonic imaging, as taught by the present inventions, the motion of the model surface may exhibit characteristics common to a linear dynamical system. Normal model operation is typically in the linear, small displacement (or small curvature) region. In one embodiment, the motion of the model is stiffness controlled. Therefore any resonance in the system occurs at a much higher frequency than that at which the external, image-derived force oscillates. Because of the difficulty of setting the elastic and mass parameters correctly, one embodiment employs non-purely-elastic characteristics for the elastic connectors, that is, when the connectors stretch or bend beyond a certain point the proportionality factor determining the return force is increased, avoiding an excessively large deformation. The model can utilize either linear or non-linear elastic connectors; the latter will tend to limit errors in the shape and thus may be preferred.

It may not be necessary for the present inventions to estimate the cardiac wall locations with extreme accuracy. The model displays the shape, motion and orientation of the heart. Proper cardiac analysis does not require exact numerical parameters from the model. Thus heart stroke volume calculations can be performed off-line using different images, the acquisition of which may be guided by the state of the model described here.

In another embodiment the contraction wave propagating through the myocardium is modeled as a driving force of the system. This may be done using surface EKG data since the location of the pacemaker cells can be defined in terms of the model. Such a feature may add to the complexity of the computations, but may be useful in predicting heart motion.

The displayed image can be generated responsive to combinations of the processed return echoes and the model. In one embodiment the model directly generates a displayed real time 3D image of the object, where the model is updated as described above. In another embodiment the real time 3D display is derived from model regions where the error is acceptable and from real time processed return echoes for the remaining regions of the object display. In yet another embodiment portions of the real time 3D image are generated from the processed return echoes where they are available and remaining regions of the displayed object are determined from the model. In still another embodiment, the displayed model is superimposed over the high resolution biplane image (including two orthogonal or non-orthogonal planes). This feature may be useful to guide probe and plane adjustments (serving as a preview image) and help the user visualize the heart motion around the two displayed planes.

In yet another embodiment where the model determines portions of the object to be insonified (as described above) with two-way beams (wherein both the transmit and receive beams provide high spatial resolution) and portions to be insonified with one-way beams (wherein only the receive beams are of high resolution while the transmit beam is sufficiently broad to allow receive beam multiplexing), the image is displayed directly responsive to the return echoes. In this display mode it may not be necessary to display the animated model since the ultrasound image may be updated at full frame rate with high resolution (i.e., low side lobe level) imaging directed to the portions of the source volume containing the anatomical features of interest. It may also be possible to detect the portions of highest side lobe energy interference simply because the model will not predict the observations well in such regions.

In a related embodiment, the insonified object is displayed as a translucent or semi-transparent graphic using the techniques described herein, with various small high-resolution, full frame rate images superimposed on the object image. The small image can be rendered based on the return echoes directly or the return echoes can update the model and the updated model rendered. The superimposed images can be planar or 3D.

In other embodiments the invention further includes an output from a Doppler range gate that shows the position in space where blood velocity information is collected. The blood velocity information is displayed as a separate image in which the Doppler spectrum is mapped against time. A deviation of the frequency from a zero value shows the mean blood velocity and the width of the Doppler spectrum indicates the presence of turbulent or non-laminar blood flow. It may also be advantageous to move the range gate in space using positional information from the model, thus tracking the blood flow from a particular point in space relative to a heart valve, as described below.

For example, the heart mitral valve can be rendered in a high-resolution, full frame rate mode based on the ultrasound return echoes, while the general outline of the heart walls is rendered in a transparent or semi-transparent image relative to the mitral valve. (The heart walls are imaged at a lower rate than the mitral valve region). The ultrasound imaging rate is sufficient to show real time motion of the valve. Blood flow into and out from the valve can be rendered using color flow mapping, a known technique in which each voxel is colored to encode the instantaneous mean Doppler shift, which indicates blood velocity, or with a spectral Doppler gate that determines the spectrum of the blood. This feature of one or more embodiments of the inventions is particularly useful for diagnosing mitral valve prolapse conditions.

In still another embodiment the object or source volume is insonified by imaging regions of the object according to a predetermined pattern. A cyclical scanning pattern directs the ultrasonic energy to object regions, returning to the initial region after scanning the desired object regions.

The teachings of the inventions can also be applied to a 2D array, with the scan lines in two dimensions imaged and processed to update the object model as described above.

Figure 2:
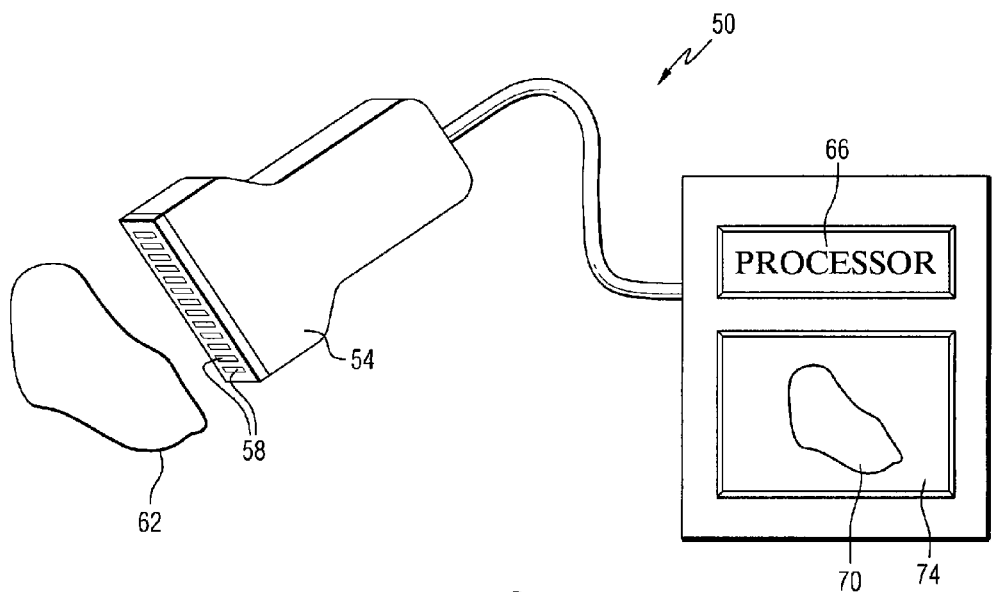
FIG. 2 illustrates an ultrasonic system according to the teachings of the inventions.

FIG. 2 illustrates an ultrasound imaging system 50 to which the teachings of the present inventions can be applied. The system 50 includes a probe 54 further including a plurality of ultrasound transducers 58 for transmitting and receiving ultrasound energy during a scan of an object 62. A processor 66 implementing the teachings of the inventions processes return echoes received by the transducers 58 to construct an image 70 on a display 74. The processor 66 generates the image based on the return echoes and the deformable model of the object as described above.

Figure 3:
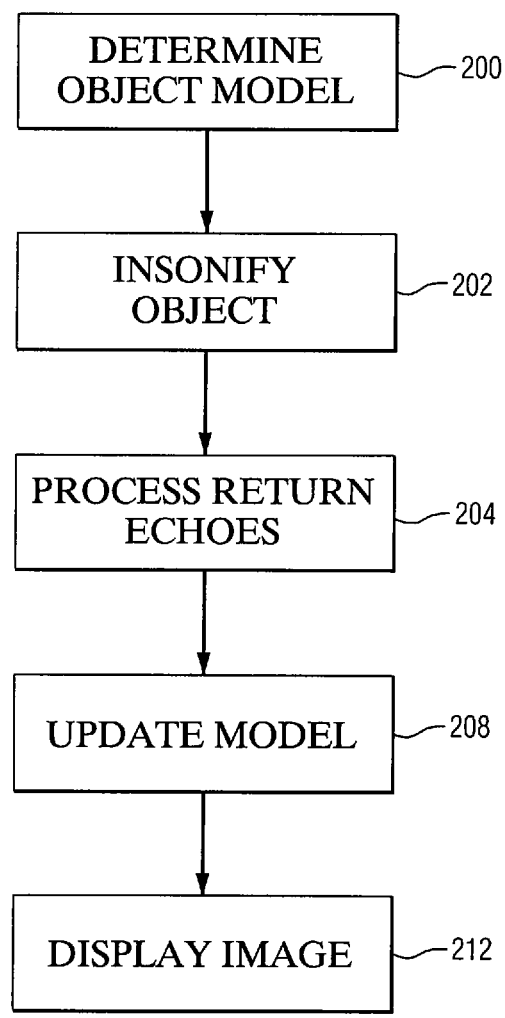
FIG. 3 illustrates a flow chart of processing steps according to one embodiment of the invention.

FIG. 3 illustrates a flow chart illustrating steps associated with one embodiment of the invention. At a step 200 a model of the object (source volume) is determined; preferably the model comprises a deformable model. The object is insonified at a step 202 and return echoes are processed at a step 204. The model is updated at a step 208 responsive to the return echoes. At a step 212 an image is generated and displayed responsive to the updated model. According to another embodiment, portions of the displayed image are responsive to the model and portions thereof are responsive to the return echoes.

In another embodiment, the ultrasonic scan rate is responsive to the time derivative of the motion of the object, e.g., the beating heart. That is, as the time derivative increases the scan rate increases. This feature permits better tracking of the object deformable model with the motion of the heart.

Persons skilled in the art will recognize that an apparatus, such as a data processing system, including a CPU, memory, I/O, program storage, a connecting bus, and other appropriate components, could be programmed or otherwise designed to facilitate the practice of the method embodiments of the invention. Such a system would include appropriate program modules for executing the methods of these embodiments, with a technical effect of rendering an image (referred to as a hybrid image) of an insonified object using both a model of the object and the return echoes from the object.

In another embodiment, an article of manufacture, such as a pre-recorded disk or other similar computer program product, for use with a data processing system, includes a storage medium and a program recorded thereon for directing the data processing system to facilitate the practice of the methods of the inventions. Such apparatus and articles of manufacture also fall within the spirit and scope of the inventions.

The inventions have been described in the general context of computer-executable instructions, such as program modules, executed by a computer. Generally, program modules include routines, programs, objects, components, data structures, etc. that perform particular tasks or implement particular abstract data types. For example, the software programs that underlie the inventions can be coded in different languages, for use with different processing platforms. In the description that follows, examples of the inventions are described in the context of a web portal that employs a web browser. It will be appreciated, however, that the principles that underlie the inventions can be implemented with other types of computer software technologies as well.

Moreover, those skilled in the art will appreciate that the invention embodiments may be practiced with other computer system configurations, including hand-held devices, multiprocessor systems, microprocessor-based or programmable consumer electronics, minicomputers, mainframe computers, and the like. The embodiments may also be practiced in a distributed computing environment where tasks are performed by remote processing devices that are linked through a communications network. In the distributed computing environment, program modules may be located in both local and remote computer storage media including memory storage devices. These local and remote computing environments may be contained entirely within the locomotive, or within adjacent locomotives in consist or off-board in wayside or central offices where wireless communications are provided between the computing environments.

Although the embodiments of the invention have been described with respect to cardiac imaging, the teachings are applicable to other body organs and other volumetric objects, especially those in motion where a high frame rate visualization (shape model) is desired. Also, because the heart is essentially a pump, visualization of its mechanical properties is often important for proper diagnosis. Motion depiction is often an important component of that diagnosis.

While the various embodiments of the invention have been described in what is presently considered to be a preferred embodiment, many variations and modifications will become apparent to those skilled in the art. For example, although described in the context of imaging a heart, the teachings of the inventions are also applicable to imaging of other organs or mechanical apparatuses, especially organs or mechanical apparatuses that include moving components. The imaging techniques can be applied to non-destructive analysis of an apparatus, for example a pump, to determine whether it is operating properly. Accordingly, it is intended that the inventions not be limited to the specific illustrative embodiments but should be interpreted within the full spirit and scope of the appended claims.

This written description of the embodiments of the invention uses examples to disclose the inventions, including the best mode, and also to enable any person skilled in the art to make and use the inventions. The patentable scope of the inventions is defined by the claims, and may include other examples that occur to those skilled in the art. Such other examples are intended to be within the scope of the claims if they have structural elements or process steps that do not differ from the literal language of the claims, or if they include equivalent structural elements or process steps with insubstantial differences from the literal language of the claims.

What is claimed is:

1. A method for producing a three-dimensional image of an object, comprising:
    insonifying one or more regions of the object from source transducers external to the object using ultrasound energy;
    receiving return echoes from the object at receiving transducers external to the object;
    determining an error between image information that corresponds to at least the insonified regions of the object and is determined from the return echoes, and further image information that corresponds to the same regions and is derived from a deformable model echoes representative of the object;
    updating at least a portion of the model corresponding to the insonified regions of the object based on the return echoes and one or more other portions of the model based on a determined dynamics of the model responsive to the return echoes;
    wherein the dynamics of the deformable model provide an instantaneous condition of one or more mass elements and connectors between the mass elements in the deformable model based on the updates from the insonified regions;
    determining a beam steering direction using feedback from the updated model so as to identify and insonify one or more of the regions of the object where the determined error is higher than in other regions of the object and receiving further return echoes;
    generating a hybrid image of the object comprising object regions responsive to the updated model of the object and object regions responsive to the further return echoes.

2. The method of claim 1 wherein the model is responsive to the return echoes from each scan line of the object.

3. The method of claim 1 further comprising determining an error between the hybrid image of the object and the further return echoes received from the one or more regions of the object, wherein the step of insonifying comprises insonifying the one or more regions to reduce the error.

4. The method of claim 1 wherein the step of generating the hybrid image comprises generating a bi-plane image responsive to the return echoes and generating an hybrid image of the object responsive to the model.

5. The method of claim 1 wherein the step of generating the hybrid image comprises generating a bi-plane image responsive to the return echoes and generating the hybrid image of the object having regions responsive to the model and regions responsive to the return echoes.

6. The method of claim 1 wherein the step of generating the hybrid image further comprises generating images at a rate of 30 frames per second.

7. The method of claim 1 wherein the deformable model further comprises an external field, and wherein the external field is generated responsive to the return echoes for modifying the model, and wherein the influence of the external field on the model decays with time.

8. The method of claim 7 wherein the object comprises a heart, and wherein a decay rate of the external field is less than a heart beat cycle.

9. The method of claim 1 wherein the step of insonifying regions of the object further comprises insonifying regions of the object along a scan line, and wherein the step of generating the hybrid image further comprises generating an image of the object including object regions proximate the scan line.

10. The method of claim 9 wherein the object regions proximate the scan line further comprise mass elements and connectors representing the object regions proximate the scan line.

11. The method of claim 1 wherein the steps of insonifying regions of the object and receiving return echoes further comprise using multiplexed ultrasound energy.

12. The method of claim 1 wherein the model further permits representation of rotation of the object.

13. The method of claim 1 further comprising a step of determining a velocity of moving particles within the regions and displaying velocity information.

14. The method of claim 13 wherein a location of the moving particles is determined responsive to the model.

15. The method of claim 1 further comprising generating a real time three-dimensional image of the object.

16. A method for rendering a heart image, comprising:
determining a deformable model that describes characteristics of a heart;
insonifying regions of the heart with ultrasonic energy; receiving return echoes from the insonified regions;
determining an error between image information that corresponds to at least the insonified regions of the heart and is determined from the return echoes, and further image information that corresponds to the same regions and is derived from the deformable model;
updating at least a portion of the model corresponding to the insonified regions of the heart based on the return echoes and one or more other portions of the model based on a determined dynamics of the model responsive to the return echoes;
wherein the dynamics of the deformable model provide an instantaneous condition of one or more mass elements and connectors between the mass elements in the deformable model based on the updates from the insonified regions;
determining a beam steering direction using feedback from the updated model so as to identify and insonify one or more regions of the object heart where the determined error is higher than in other regions of the object heart and receiving further return echoes; and
producing the heart image responsive to one or more of the updated model and the further return echoes.

17. The method of claim 16 wherein the step of producing further comprises producing regions of the image responsive to the return echoes and other regions of the image responsive to the updated model.

18. The method of claim 16 further comprising processing the return echoes to generate a potential field representative of the return echoes, wherein the step of creating the updated model further comprises applying the potential field to the model to create the updated model.

19. The method of claim 18 wherein the potential field generated by the return echoes decays with time.

20. The method of claim 19 wherein a rate of the decay permits application of the potential field to the model during an interval shorter than a heat beat.

21. The method of claim 16 wherein the step of insonifying further comprises insonifying regions of the heart with ultrasonic energy produced by a one-dimensional array of ultrasonic transducers or by a two-dimensional array of ultrasonic transducers.

22. The method of claim 16 wherein the step of insonifying comprises insonifying the regions of the heart with ultrasonic energy using a multiplexed ultrasonic energy beam.

23. The method of claim 16 wherein the step of insonifying further comprises insonifying regions of the heart responsive to a heart's contraction wave.

24. The method of claim 16 wherein the step of creating further comprises applying the potential field to the model describing characteristics of the heart in the insonified regions.

25. The method of claim 16 further comprising determining a difference between the image and the return echoes, wherein the step of insonifying regions of the heart is responsive to the difference to reduce the difference.

26. The method of claim 25 wherein the step of insonifying further comprises steering the ultrasonic energy to insonify regions of the heart to reduce the difference.

27. The method of claim 16 wherein the step of insonifying further comprises selecting ultrasonic beam characteristics to insonify a desired region of the heart.

28. The method of claim 16 wherein the dynamics of the model depicts angular velocity of the heart.

29. The method of claim 16 wherein the step of producing further comprises producing a biplane image of the heart and superimposing the heart image over the biplane image.

30. The method of claim 16 further comprising a step of determining a velocity of moving particles within the regions and displaying velocity information.

31. The method of claim 30 wherein a location of the moving particles is determined responsive to the model.

32. The method of claim 16 further comprising processing the return echoes to generate a potential field representative of the return echoes, wherein the step of creating the updated model further comprises applying the potential field to the model to create the updated model, and wherein the model comprises state equations having state variables and derivatives of the state variables, and wherein the step of creating comprises applying the potential field to the state equations to update the state variables and the derivatives of the state variables, and wherein the step of producing further comprises producing the heart image responsive to the state variables and the derivatives of the state variables.

33. A method for providing a three-dimensional image of an object, comprising:
insonifying regions of the object using ultrasound energy; using a model of the object for imaging;

determining an error between image information that corresponds to at least the insonified regions of the object and is determined from the return echoes, and further image information that corresponds to the same regions and is derived from a deformable model corresponding to the object;

updating at least a portion of the model corresponding to the insonified regions of the object based on the return echoes and one or more other portions of the model based on a determined dynamics of the model responsive to the return echoes;

wherein the dynamics of the deformable model provide an instantaneous condition of one or more mass elements and connectors between the mass elements in the deformable model based on the updates from the insonified regions;

determining a beam steering direction using feedback from the updated model so as to identify and insonify one or more regions of the object where the determined error is higher than in other regions of the object and receiving further return echoes; and generating a hybrid image of the object responsive to the updated model of the object or responsive to a combination of the further return echoes and the updated model.

34. The method of claim 33 wherein the step of generating an hybrid image further comprises generating an image at a desired frame rate, and wherein the step of updating a portion of the model executes more frequently than the frame rate.

35. The method of claim 33 further comprising determining a difference between the image and the return echoes, wherein the step of insonifying regions of the object is responsive to the difference by steering the ultrasonic energy to insonify regions of the object to reduce the difference.

36. The method of claim 33 wherein the step of updating the portion of the model further comprises applying a potential field derived from the return echoes to the model.

37. The method of claim 33 wherein the method further comprises generating a real time three-dimensional image of the object.

38. A method for producing a three-dimensional image of an object, comprising:

insonifying a first region of the object with ultrasonic energy;

receiving return echoes from the first region of the object;

determining an error between image information that corresponds to at least the insonified regions of the object and is determined from the return echoes, and further image information that corresponds to the same regions and is derived from a deformable model corresponding to the object;

producing an updated model, wherein at least a portion of the model corresponding to the insonified regions of the object is updated based on the return echoes and one or more other portions of the model are updated based on a determined dynamics of the model responsive to the return echoes;

wherein the dynamics of the deformable model provide an instantaneous condition of one or more mass elements and connectors between the mass elements in the deformable model based on the updates from the insonified regions;

determining a beam steering direction using feedback from the updated model to identify and insonify a second region of the object where the determined error is higher than in other regions of the object, and wherein the second region is insonified at a higher rate than the first region;

receiving further return echoes from the second region of the object; and displaying an image of the object comprising the first region responsive to the updated model and the second region responsive to the further return echoes.

39. The method of claim 38 wherein the step of displaying further comprises the first region displayed such that the second region is visible through the first region.

40. The method of claim 38 wherein the object comprises a heart, the first region comprises a heart myocardium and the second region comprises a heart valve.

41. The method of claim 40 further comprising determining blood flow through the valve, wherein the step of displaying the image further comprises displaying the blood flow.

42. The method of claim 38 wherein the step of displaying further comprises displaying an image of the object comprising the first region responsive to the updated model and the second region responsive to the updated model farther responsive to the return echoes.

43. The method of claim 38 wherein the step of displaying the image further comprises displaying the image at a rate of 30 frames per second, wherein motion of the second region is displayed in real time.

44. The method of claim 38 wherein a resolution of the second region is greater than a resolution of the first region.

45. The method of claim 38 wherein the deformable model further comprises an external field, and wherein the external field is responsive to the return echoes from the object, and wherein the influence of the external field on the model decays with time.

46. The method of claim 38 wherein the deformable model further comprises an external field, and the step of producing an updated model further comprises applying the external field to the first region of the model of the object, and wherein the influence of the external field on the model decays with time.

47. The method of claim 38 wherein the steps of insonifying the first and the second regions further comprise insonifying the first and the second regions using multiplexed ultrasound energy.

48. The method of claim 38 wherein the method further comprises generating a real time three-dimensional image of the object.

49. A method for providing a three-dimensional image of a moving object, comprising:

insonifying regions of the object at a scan rate with ultrasonic energy;

determining an error between image information that corresponds to at least the insonified regions of the object and is determined from the return echoes, and further image information that corresponds to the same regions and is derived from a deformable model representative of at least a portion of the object;

updating at least a portion of the model corresponding to the insonified regions of the object based on the return echoes and one or more other portions of the model based on a determined dynamics of the model responsive to the return echoes;

wherein the dynamics of the deformable model provide an instantaneous condition of one or more mass elements and connectors between the mass elements in the deformable model based on the updates from the insonified regions;

determining a time derivative of motion of the object;

modifying the scan rate responsive to the time derivative;
determining a beam steering direction using feedback from the updated model to identify and insonify one or more regions of the object where the determined error is higher than in other regions of the object using the modified scan rate and receiving further return echoes; and
generating an image of the object responsive to the updated model of the object or responsive to a combination of the further return echoes and the updated model.

50. An ultrasonic imaging apparatus for producing an image of an object, the apparatus comprising:
a plurality of ultrasonic transducers for generating ultrasonic energy, for receiving return echoes from the object and for generating signals responsive to the return echoes;
a processor configured to:
determine an error between image information that corresponds to at least the insonified regions of the object and is determined from the return echoes, and further image information that corresponds to the same regions and is derived from a deformable model representative of the object;
update at least a portion of the model corresponding to the insonified regions of the object based on the return echoes and one or more other portions of the model based on a determined dynamics of the model responsive according to the signals;
wherein the dynamics of the deformable model provide an instantaneous condition of one or more mass elements and connectors between the mass elements in the deformable model based on the updates from the insonified regions;
determine a beam steering direction using feedback from the updated model to identify and insonify one or more regions of the object where the determined error is higher than in other regions of the object; and
a display for displaying a hybrid image of the object responsive to one or more of the updated object model and signals responsive to return echoes received from the one or more regions of the object.

51. The ultrasonic imaging apparatus of claim 50 wherein the plurality of ultrasonic transducers comprises a one dimensional array of transducers or a two-dimensional array of transducers.

52. The ultrasonic imaging apparatus of claim 50 wherein the processor modifies at least one of the mass elements and the connectors responsive to the signals.

53. The ultrasonic imaging apparatus of claim 50 wherein the plurality of ultrasonic transducers receive echoes from a scan line of the object, and wherein the processor updates the portion of the object model according to each scan line.

54. An ultrasonic imaging apparatus for producing a sequence of images of an object, the apparatus comprising:
a plurality of ultrasonic transducers for generating ultrasonic energy, for receiving return echoes from the object and for generating signals responsive to the return echoes;
a processor configured to:
generate a deformable model representing the object;
determine an error between image information that corresponds to at least insonified regions of the object and is determined from the return echoes, and further image information that corresponds to the same regions and is derived from the model;
update the model corresponding to the insonified regions of the object based on the return echoes and one or more other portions of the model based on a determined dynamics of the model responsive to the signals to produce an updated model;
wherein the dynamics of the deformable model provide an instantaneous condition of one or more mass elements and connectors between the mass elements in the deformable model based on the updates from the insonified regions;
determine a beam steering direction using feedback from the updated model to identify and insonify one or more regions of the object where the determined error is higher than in other regions of the object and receive further return echoes; and
a display for displaying a first image of the object including a portion of the first image based on the updated model and a portion of the first image based on one or more of the signals and the further return echoes, and wherein at least a portion of a second image of the object comprises the updated model.

55. The ultrasonic imaging apparatus of claim 54 wherein the plurality of ultrasonic transducers comprises a one dimensional array of transducers or a two-dimensional array of transducers.

56. The ultrasonic imaging apparatus of claim 54 wherein the processor further updates at least one of the mass elements and the connectors according to the signals.

57. The ultrasonic imaging apparatus of claim 54, wherein the step of insonifying comprises insonifying selected regions of the object to reduce the error.

58. The ultrasonic imaging apparatus of claim 54 wherein the first and the second images each comprise a first region responsive to the signals and a second region responsive to the model.

59. The ultrasonic imaging apparatus of claim 54 wherein a first portion of the second image is responsive to the updated model and a second portion of the second image is responsive to the signals.

60. A non-transitory computer readable storage medium that stores instructions executable by one or more processors to perform a method for producing a real time image of an object, comprising:
insonifying regions of the object using a source transducer with ultrasonic energy and receiving return echoes from the object using a receive transducer;
determining an error between image information that corresponds to at least insonified regions of the object and is determined from the return echoes, and further image information that corresponds to the same regions and is derived from a deformable model;
updating at least a portion of the model corresponding to the insonified regions of the object based on the return echoes and one or more other portions of the model based on a determined dynamics of the model responsive to the return echoes;
wherein the dynamics of the deformable model provide an instantaneous condition of one or more mass elements and connectors between the mass elements in the deformable model based on the updates from the insonified regions;
determining a beam steering direction using feedback from the updated model so as to identify and insonify one or more regions of the object where the determined error is higher than in other regions of the object and receiving further return echoes;
generating a hybrid image of the object comprising object regions responsive to the updated model of the object and object regions responsive to the further return echoes received from the one or more regions of the object where the determined error is higher than in other regions of the object.

\* \* \* \* \*